US00PP16058P2

(12) United States Plant Patent
Kester

(10) Patent No.: US PP16,058 P2
(45) Date of Patent: Oct. 25, 2005

(54) ***CHRYSANTHEMUM* PLANT NAMED 'LEXY'**

(50) Latin Name: *Chrysanthemum Dendranthema Indicum*
Varietal Denomination: Lexy

(75) Inventor: Josef A. J. Kester, De Lier (NL)

(73) Assignee: ides Goldstock Breeding B.V., De Lier (NL)

( * ) Notice: Subject to any disclaimer, the term of this patent is extended or adjusted under 35 U.S.C. 154(b) by 110 days.

(21) Appl. No.: 10/756,610

(22) Filed: Jan. 13, 2004

(51) Int. Cl.[7] ..... A01H 5/00
(52) U.S. Cl. ..... Plt./290
(58) Field of Search ..... Plt./290

*Primary Examiner*—Anne Marie Grunberg
*Assistant Examiner*—Annette H Para
(74) *Attorney, Agent, or Firm*—Mark P. Bourgeois

(57) ABSTRACT

A new cultivar of *Chrysanthemum* plant named 'Lexy' that is characterized by orange pompon flowers with a dark center, a strong and uniform stem, dark green leaves, good life as a cut flower and a large quantity of flowers at the top of the plant. In combination, these traits set 'Lexy' apart from other known existing varieties of *Chrysanthemum*.

1 Drawing Sheet

Botanical classification: *Chrysanthemum Dendranthema Indicum.*
Variety denomination: 'Lexy'.

BACKGROUND OF THE INVENTION

The present invention relates to a new and distinct cultivar of *Chrysanthemum* plant botanically known as *Chrysanthemum Dendranthema Indicum* and hereinafter referred to by the cultivar name 'Lexy'.

The new cultivar is the product of a breeding program conducted by the inventor in a cultivated area of De Lier, The Netherlands. The objective of the breeding program is to develop new *Chrysanthemum* cultivars with interesting and unique flower colors and shapes that are suitable for high volume greenhouse production.

'Lexy' is a hybrid that originated from the induced hydribization of the female or seed parent *Chrysanthemum* 'Restone' (not patented) and the male or pollen parent *Chrysanthemum* 'Ariane' (not patented). The cultivar 'Lexy' was selected by the inventor in May of 2001 as a single plant within the progeny of the stated cross in a controlled environment of De Lier, The Netherlands.

Asexual reproduction by terminal cuttings of the new cultivar 'Lexy' were performed in August 2001 in De Lier, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Chrysanthemum* cultivar 'Lexy'. These traits in combination distinguish 'Lexy' as a new and distinct cultivar apart from other known varieties of *Chrysanthemum.*

1. *Chrysanthemum* 'Lexy' exhibits an orange pompon flower with a dark center.
2. *Chrysanthemum* 'Lexy' exhibits a strong and uniform stem.
3. *Chrysanthemum* 'Lexy' exhibits dark green leaves.

4. *Chrysanthemum* 'Lexy' exhibits good life as a cut flower.
5. *Chrysanthemum* 'Lexy' exhibits a large quantity of flowers on the top.
6. *Chrysanthemum* 'Lexy' exhibits a short crop time.

The closest comparison varieties are *Chrysanthemum* 'Deliflame' (not patented) and *Chrysanthemum* 'Baltimore' (not patented). 'Lexy' is different than 'Deliflame' in that 'Lexy' has a longer response time, smaller flowers, a stronger more uniform stem and smaller leaves. 'Lexy' is different than 'Baltimore' in that 'Lexy' is not resistant to white rust, has smaller leaves and more uniform stems. The leaves of 'Baltimore' are susceptible to yellowing while the leaves of 'Lexy' are not. The flowers of 'Baltimore' are gold with a light center. The flowers of 'Lexy' are orange with a dark center.

'Lexy' is different than the female parent 'Restone' in that 'Lexy' has larger flowers, smaller leaves and more uniform stems. The leaves of 'Restone' are susceptible to yellowing while the leaves of 'Lexy' are not. The flowers of 'Restone' are gold with a light center. The flowers of 'Lexy' are orange with a dark center.

'Lexy' is different than the male parent 'Ariane' in that 'Lexy' has shorter more uniform stems and a longer response time. 'Ariane' is resistant to white rust while 'Lexy' is not. The flowers of 'Ariane' are pale pink with a dark center. The flowers of 'Lexy' are orange with a dark center.

BRIEF DESCRIPTION OF THE DRAWING

The accompanying photograph illustrates the distinguishing traits of *Chrysanthemum* 'Lexy'. The plant in the photograph shows an overall view of a 10 week old plant. The photograph was taken using conventional techniques and although colors may appear different from actual colors due to light reflectance it is as accurate as possible by conventional photographic technique.

BOTANICAL DESCRIPTION OF THE PLANT

The following is a detailed description of the new *Chrysanthemum* cultivar named 'Lexy'. Data was collected in De Lier, The Netherlands from 10 week glass greenhouse grown plants. The time of year was June and the average temperature was 18.5° Centigrade during the day and night. The light level was natural outdoor light. Photoperiodic treatments of 2 weeks of long days and 8 weeks of short days were used. Alar growth retardant was used 4 times at a rate of 2 grams per liter. Color determinations are in accordance with The Royal Horticultural Society Colour Chart 2001 edition, except where general color terms of ordinary dictionary significance are used.

'Lexy' has not been tested under all possible conditions and phenotypic differences may be observed with variations in environmental, climatic, and cultural conditions, however, without any variance in genotype.

Botanical classification: *Chrysanthemum Dendranthema Indicum* 'Lexy'.
Annual or perennial: Perennial.
Parentage: 'Lexy' is a hybrid plant that resulted from the induced hybridization of the following parent plants:
*Female parent.*—*Chrysanthemum* 'Restone'.
*Male parent.*—*Chrysanthemum* 'Ariane'.
Vigor: Moderate to High.
Growth habit: Upright.
Plant shape: Columnar.
Height: 79 cm. in height.
Width: 19.5 cm. in width.
Hardiness: USDA Zone 7.
High temperature tolerance: 35 degrees Centigrade.
Propagation: Terminal cuttings.
Time to initiate roots in summer: 5 days to produce roots on an initial cutting.
Time to initiate roots in winter: 6 days to produce roots on an initial cutting.
Time to produce a rooted cutting or liner in summer: 11 days.
Time to produce a rooted cutting or liner in winter: 15 days.
Summer crop time: From a rooted cutting, 9.5 weeks are required to produce a finished flowering plant.
Winter crop time: From a rooted cutting, 15 weeks are required to produce a finished flowering plant.
Root system: Fine and fibrous.
Stem:
*Branching habit.*—Moderate branching.
*Average number of lateral branches.*—1.
*Pinching.*—No.
*Lateral branch diameter.*—6.5 mm. in diameter.
*Lateral branch length.*—79 cm. in length.
*Stem strength.*—High.
*Stem color.*—144A.
*Pubescence.*—Strong, length: 0.5 mm, color: 157C.
*Internode length.*—2.8 cm. between nodes.
*Shape.*—Rounded, slightly angular.
Foliage:
*Texture.*—Dull, slightly rough.
*Leaf arrangement.*—Alternate.
*Compound or single.*—Single.
*Quantity of leaves per lateral branch.*—28.
*Leaf shape.*—Pinnatifid to Pinnatisect.
*Leaf apex.*—Acute.
*Leaf base.*—Attenuate.
*Leaf length.*—10.7 cm. in length.
*Leaf width.*—6.8 cm. in width.
*Pubescence.*—Slight, both sides, length: 0.2 mm, color: 155D.
*Leaf margin.*—Serrate, 3 teeth per 2 cm.
*Sinuses.*—Parallel to convergent.
*Young leaf color* (*lower surface*).—138A to 138B.
*Young leaf color* (*upper surface*).—137B.
*Mature leaf color* (*lower surface*).—137B to 137C.
*Mature leaf color* (*upper surface*).—137A to 139A.
*Vein color* (*lower surface*).—138B.
*Vein color* (*upper surface*).—138B to 138C.
*Leaf attachment.*—Petiolate.
*Petiole dimensions.*—2.2 cm in length and 3.0 mm. in diameter.
*Petiole color.*—138B.
*Durability of foliage to stress.*—High.
*Stipules.*—2 at the base of each petiole, 5.5 mm in length, 4 mm in width, color upper side 137A to 139A, color lower side 138A to 138B.
Flower:
*Inflorescence type.*—Terminal capitulua arranged in panicles.
*Inflorescence form.*—Terminal capitulua consisting mainly of ray florets, very few disc florets.
*Flowering habit.*—Continuous.
*Quantity of flowers per lateral stem.*—11.
*Quantity of flower buds per lateral stem.*—11.
*Quantity of flowers and buds per plant.*—22.
*Flowering season.*—Fall.
*Response time.*—50 days on average.
*Fragrance.*—Faint.
*Bud length.*—6 mm. in length.
*Bud diameter.*—1 cm. in diameter.
*Bud shape.*—Globose.
*Bud color.*—143A to 143C with a yellow-green top 144A and grey-orange margins 167D.
*Flower aspect.*—Upright to slightly outward.
*Flower dimensions.*—4.1 cm. in diameter and 2.1 cm. in height.
*Disc diameter.*—3 mm.
*Receptacle diameter.*—1.6 cm.
*Receptacle height.*—2 mm.
*Flower longevity.*—Lasts approximately 14 days on plant or as a cut flower.
*Ray floret number.*—Average 200.
*Ray floret arrangement.*—18 overlapping rows.
*Ray floret appearance.*—Dull.
*Ray floret aspect.*—Flat.
*Ray floret texture.*—Smooth.
*Ray floret shape.*—Ovate.
*Ray floret margin.*—Entire.
*Ray floret apex.*—Obtuse.
*Ray floret base.*—Attenuate.
*Ray floret dimensions.*—1.8 cm. in length, 7 mm. in width.
*Ray floret color when opening* (*upper side*).—23A to 23B with a yellow base 7B.
*Ray floret color when opening* (*under side*).—23C with a green-yellow base 1B and an orange margin at the apex. 25A.
*Ray floret color fully open* (*upper side*).—21A with a yellow base 7B to 7C.
*Ray floret color fully open* (*under side*).—23C to 24C with yellow base 1B.
*Ray floret color fading to.*—Not fading.
*Disc floret number.*—Average 12.
*Disc floret arrangement.*—Center of receptacle.
*Disc floret shape.*—Tubular.
*Disc floret apex.*—5 lobed, each lobe having an acute apex.

*Disc floret dimensions.*—4 mm. in length, 1.0 mm. in width at apex, 0.75 mm in width at base.
*Disc floret color when opening.*—145B.
*Disc floret color fully open* (*at apex*).—153C to 153D.
*Disc floret color fully open* (*middle*).—153D.
*Disc floret color fully open* (*base*).—145B.
*Disc floret color fading.*—Not fading.
*Sel-cleaning or persistent.*—Persistent.

Phyllaries:
*Phyllary number.*—32 on average.
*Phyllary arangement.*—3 rows.
*Phyllary appearance.*—Dull with transparent margins, strongly pubsecent, pubescence 0.5 mm in length and 155D in color.
*Phyllary shape.*—Ovate to oblong.
*Phyllary apex.*—Obtuse.
*Phyllary base.*—Broad cuneate.
*Phyllary dimensions.*—7 mm. in length and 3 mm. in width.
*Phyllary color* (*upper side*).—143A.
*Phyllary color* (*under side*).—137A.

Peduncle:
*Peduncle length terminal peduncle.*—5.1 cm.
*Peduncle length fourth peduncle.*—7.1 cm.
*Peduncle length seventh peduncle.*—8.7 cm.
*Peduncle diameter.*—2 mm.
*Peduncle angle.*—20°.
*Peduncle color.*—138A.
*Peduncle strength.*—Strong.
*Peduncle surface.*—Dull.
*Peduncle pubescence.*—Strong, 0.5 mm in length, 155D in color.

Reproduction organs:
*Stamen number.*—5.
*Anther shape.*—Lanceolate.
*Anther dimensions.*—1.5 mm. in length.
*Anther color.*—153C to 153D.
*Amount of pollen.*—Moderate.
*Pollen color.*—14A.
*Pistil number.*—1 in number.
*Pistil dimensions.*—5 mm. in length.
*Stigma shape.*—Cleft.
*Stigma color.*—153D.
*Style length.*—4 mm.
*Style color.*—145C.
*Ovary color.*—145D.

Seed: Seed production has not been observed.

Disease resistance: Susceptible to white rust.

It is claimed:

1. A new and distinct variety of *Chrysanthemum* plant named 'Lexy' as described and illustrated.

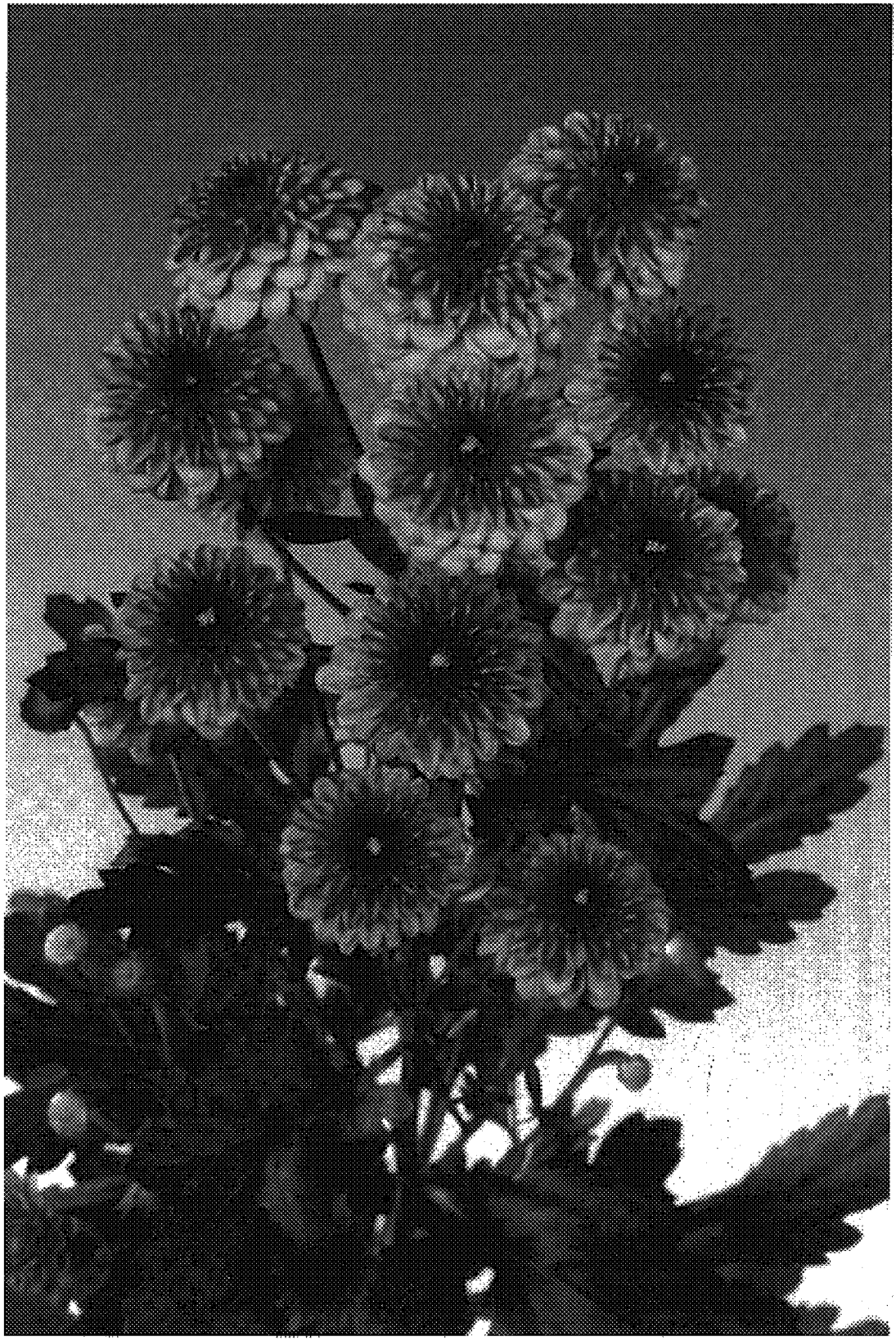

* * * * *